United States Patent
Peng et al.

(10) Patent No.: US 11,912,639 B2
(45) Date of Patent: Feb. 27, 2024

(54) PROCESSES FOR PRODUCING Z-1,1,1,4,4,4-HEXAFLUOROBUT-2-ENE AND INTERMEDIATES FOR PRODUCING SAME

(71) Applicant: THE CHEMOURS COMPANY FC, LLC, Wilmington, DE (US)

(72) Inventors: Sheng Peng, Hockessin, DE (US); Allen Capron Sievert, Elkton, MD (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 109 days.

(21) Appl. No.: 17/601,512

(22) PCT Filed: Apr. 3, 2020

(86) PCT No.: PCT/US2020/026671
§ 371 (c)(1),
(2) Date: Oct. 5, 2021

(87) PCT Pub. No.: WO2020/206322
PCT Pub. Date: Oct. 8, 2020

(65) Prior Publication Data
US 2022/0194879 A1 Jun. 23, 2022

Related U.S. Application Data

(60) Provisional application No. 62/829,846, filed on Apr. 5, 2019.

(51) Int. Cl.
| | | |
|---|---|---|
| C07C 17/093 | (2006.01) | |
| C07C 17/25 | (2006.01) | |
| C07C 17/354 | (2006.01) | |
| C07C 17/269 | (2006.01) | |
| C07C 17/06 | (2006.01) | |
| C07C 17/04 | (2006.01) | |
| C07C 17/21 | (2006.01) | |
| C07C 21/22 | (2006.01) | |
| C07C 19/10 | (2006.01) | |
| C07C 17/10 | (2006.01) | |
| B01J 23/44 | (2006.01) | |

(52) U.S. Cl.
CPC .............. *C07C 17/06* (2013.01); *C07C 17/04* (2013.01); *C07C 17/10* (2013.01); *C07C 17/21* (2013.01); *C07C 17/25* (2013.01); *C07C 17/269* (2013.01); *C07C 17/354* (2013.01); *C07C 19/10* (2013.01); *C07C 21/22* (2013.01); *B01J 23/44* (2013.01)

(58) Field of Classification Search
CPC .............................. C07C 17/06; C07C 17/093
See application file for complete search history.

(56) References Cited

U.S. PATENT DOCUMENTS

| | | | | |
|---|---|---|---|---|
| 5,315,047 A | * | 5/1994 | Lui | .................... C07C 21/18 570/166 |
| 9,440,896 B2 | | 9/2016 | Peng | |
| 2008/0269532 A1 | * | 10/2008 | Swearingen | .......... C07C 17/354 570/175 |

FOREIGN PATENT DOCUMENTS

| | | | | |
|---|---|---|---|---|
| CN | 104684877 A | | 6/2015 | |
| WO | WO-9505353 A1 | * | 2/1995 | ............. C07C 19/01 |
| WO | WO-2014052695 A1 | * | 4/2014 | ............. C07C 17/25 |
| WO | 2019/23572 A1 | | 1/2019 | |

OTHER PUBLICATIONS

Hartung, J., "Synthesis by Substitution of Hydrogen", pp. 19-46, Science of Syntheses 35.1 One Saturated Carbon-Chlorine Bond.
Kolomeitsev, et al., "Two-Step Phosphorus-Mediated Substitution of Hydroxy Groups in Selected Primary Alcohols for Fluorinated Alkyl or Aryl Substituents: the Molecular Structure of 1,1-Bis(Fluorosulfonyl)-1-Fluoro-2-Phenylethane", Chem. Communi, 1998, pp. 705-706.

* cited by examiner

*Primary Examiner* — Medhanit W Bahta

(57) ABSTRACT

Processes for producing Z-1,1,1,4,4,4-hexafluorobut-2-ene and intermediates for producing same. A process for producing 2-chloro-1,1,1,4,4,4-hexafluorobutane comprises contacting 1,1,2,4,4-pentachlorobuta-1,3-diene with HF in the liquid phase in the presence of a fluorination catalyst. A process for producing 2,2-dichloro-1,1,1,4,4,4-hexafluorobutane comprises contacting 2-chloro-1,1,1,4,4,4-hexafluorobutane with a chlorine source. A process for producing 1,1,1,4,4,4-hexafluoro-2-butyne comprises contacting 2,2-dichloro-1,1,1,4,4,4-hexafluorobutane with a base. A process for producing Z-1,1,1,4,4,4-hexafluorobut-2-ene comprises contacting 1,1,1,4,4,4-hexafluoro-2-butyne with hydrogen.

16 Claims, No Drawings

PROCESSES FOR PRODUCING Z-1,1,1,4,4,4-HEXAFLUOROBUT-2-ENE AND INTERMEDIATES FOR PRODUCING SAME

CROSS REFERENCE TO RELATED APPLICATIONS

This application is a national filing under 35 U.S.C. 371 of International Application No. PCT/US2020/026671 filed Apr. 3, 2020, and claims priority of U.S. Provisional Application No. 62/829,846 filed Apr. 5, 2019, the disclosures of which are incorporated herein by reference in its entirety.

TECHNICAL FIELD

The disclosure herein relates to liquid and vapor phase processes used in producing Z-1,1,1,4,4,4-hexafluoro-2-butene and intermediates useful in its production. The disclosure further provides processes for producing 2-chloro-1,1,1,4,4,4-hexafluorobutane and 2,2-dichloro-1,1,1,4,4,4-hexafluorobutane.

BACKGROUND

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as refrigerants, cleaning agents, expansion agents for thermoplastic and thermoset foams, heat transfer media, gaseous dielectrics, aerosol propellants, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs). HFCs have zero ozone depletion potential and thus are not affected by the current regulatory phase-out known as the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus, there is a need for manufacturing processes that provide intermediates useful to produce hydrofluoroolefins and non-chlorinated hydrofluoroolefins that have low global warming potential.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

SUMMARY

The present disclosure provides processes for the production of hydrofluoroolefin Z-1,1,1,4,4,4-hexafluorobut-2-ene (Z—HFO-1336mzz, or Z-1336mzz) and intermediates useful in its production.

The present disclosure provides a process for the production of 2,2-dichloro-1,1,1,4,4,4-hexafluorobutane (HCFC-336mfa). HCFC-336mfa is produced starting from 2-chloro-1,1,1,4,4,4-hexafluorobutane (HCFC-346mdf), which is in turn produced from 1,1,2,4,4-pentachlorobuta-1,3-diene (HCC-2320az).

In some embodiments, HCFC-336mfa is used in a process to produce 1,1,1,4,4,4-hexafluoro-2-butyne, which process comprises contacting HCFC-336mfa with base. In some embodiments, 1,1,1,4,4,4-hexafluoro-2-butyne is recovered and then reacted with hydrogen to form Z-1,1,1,4,4,4-hexafluoro-2-butene.

The present disclosure provides a process for the production of Z-1,1,1,4,4,4-hexafluorobut-2-ene comprising (a) contacting 1,1,2,4,4-pentachlorobuta-1,3-diene with HF in the liquid phase in the presence of a fluorination catalyst to produce a product mixture comprising 2-chloro-1,1,1,4,4,4-hexafluorobutane; (b) contacting 2-chloro-1,1,1,4,4,4-hexafluorobutane with a chlorine source to produce a product mixture comprising 2,2-dichloro-1,1,1,4,4,4-hexafluorobutane; (c) contacting 2,2-dichloro-1,1,1,4,4,4-hexafluorobutane with base to produce a product mixture comprising 1,1,1,4,4,4-hexafluoro-2-butyne; and (d) contacting 1,1,1,4,4,4-hexafluoro-2-butyne with hydrogen to produce a product mixture comprising Z-1,1,1,4,4,4-hexafluoro-2-butene.

In some embodiments, 1,1,2,4,4-pentachlorobuta-1,3-diene (HCC-2320az, 2320az) is produced according to a process comprising dimerization of trichloroethylene (TCE). A process to produce 2320az comprises contacting TCE in the presence of a catalyst to produce a product mixture comprising 2320az.

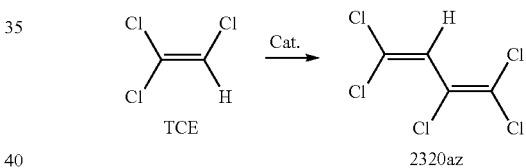

In some embodiments, the dimerization of TCE is performed in the presence of pentachloroethane ($CCl_3CHCl_2$, HCC-120), which accelerates the dimerization process.

In certain embodiments, 2320az is produced with a selectivity at least 80%; in some embodiments, selectivity is greater than 90% or greater than 95% or greater than 99% or greater than 99.5%. In certain embodiments, 2320az is recovered from the product mixture. In some embodiments, unreacted TCE is recovered and recycled.

In some embodiments, 2-chloro-1,1,1,4,4,4-hexafluorobutane (HFC-346mdf) is produced by contacting 1,1,2,4,4-pentachlorobuta-1,3-diene with hydrogen fluoride (HF) in the liquid phase in the presence of a fluorination catalyst to produce a product mixture comprising HFC-346mdf.

In the process of this disclosure, 2-chloro-1,1,1,4,4,4-hexafluorobutane is contacted with a chlorine source to produce 2,2-dichloro-1,1,1,4,4,4-hexafluoropropane (HCFC-336mfa).

The present disclosure further provides compositions produced according to the processes disclosed herein.

DETAILED DESCRIPTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

By "recovering" it is meant to sufficiently isolate the desired product to make it available for its intended use, either as a starting material for a subsequent reaction step or, in the case of recovering Z-1,1,1,4,4,4-hexafluoro-2-butene, useful, for example, as a refrigerant or foam expansion agent or solvent or fire extinguishant or electronic gas.

The details of the recovery step will depend on the compatibility of the product mixture with the reaction conditions of the subsequent reaction step. For example, if the product is produced in a reaction medium that is different from or incompatible with a subsequent reaction step, then the recovery step may include separation of the desired product from the product mixture including the reaction medium. This separation may occur simultaneously with the contacting step when the desired product is volatile under the reaction conditions. The volatilization of the desired product can constitute the isolation and thereby the recovery of the desired product. If the vapors include other materials intended for separation from the desired product, the desired product may be separated, by selective distillation, for example.

The steps for recovering the desired product from the product mixture, preferably comprise separating the desired product from catalyst or other component(s) of the product mixture used to produce the desired product or produced in the process.

The present disclosure provides, inter alia, processes to produce Z-1336mzz, and intermediates for producing Z-1336mzz. Such process may use a starting material comprising 1,1,2,4,4-pentachlorobuta-1,3-diene, which may be produced from trichloroethylene, one method as set forth herein.

Production of 1,1,2,4,4-Pentachlorobuta-1,3-Diene (2320Az)

1,1,2,4,4-pentachlorobuta-1,3-diene (HCC-2320az, or 2320az) may be produced in accordance with this disclosure by dimerization of trichloroethylene (TCE). In some embodiments, there is provided a process to produce a product mixture comprising 2320az, which process comprises contacting TCE with a dimerization catalyst at an elevated temperature.

In some embodiments, the dimerization catalyst comprises iron. An iron dimerization catalyst may comprise metallic iron from any source (including a combination of sources) and may be or comprise iron powder, iron wire, iron screen or iron turnings. The iron catalyst may also comprise an iron salt such as ferric chloride or ferrous chloride ($FeCl_3$ or $FeCl_2$, respectively).

In some embodiments, the dimerization catalyst comprises copper. A copper dimerization catalyst may comprise metallic copper from any source (including a combination of sources) and may be or comprise copper powder or copper wire, for example. The copper catalyst may also comprise a cuprous or a cupric salt such as cuprous chloride or cupric chloride ($CuCl$ or $CuCl_2$, respectively).

The process is preferably performed in an anhydrous environment. For example, when ferric chloride is used, the ferric chloride is preferably anhydrous.

In some embodiments, the dimerization catalyst has a particular concentration with respect to moles of TCE reactant used. As such, in some embodiments wherein the catalyst comprises a metallic iron catalyst, a ratio of weight of Fe wire (or Fe powder) catalyst to TCE is from about 0.0001 to about 1. In other embodiments, the weight ratio of iron catalyst to TCE is from about 0.01 to about 1.

In some embodiments, the dimerization catalyst comprises ferric chloride and the weight ratio of ferric chloride to TCE is from about 0.00001 to about 1. For example, the weight ratio of ferric chloride to TCE is from about 0.00001 to about 0.002, while in another example, the weight ratio is from about 0.00005 to about 0.001. In yet another example, a weight ratio of ferric chloride to TCE is from about 0.0001 to about 1, while in a further example, the ratio of ferric chloride to TCE is from about 0.00015 to about 1.

In some embodiments, trichloroethylene is contacted with a dimerization catalyst and pentachloroethane. Pentachloroethane (HCC-120) accelerates the reaction to produce the product mixture comprising 2320az. In certain embodiments, a weight ratio of HCC-120 to TCE is from about 0.001 to about 1. In other embodiments, the weight ratio of HCC-120 to TCE is from about 0.005 to about 1.

The dimerization of TCE is performed in at an elevated temperature, for example at a temperature in the range of about 210 to about 235° C. The temperature may be greater than 200° C. The temperature may be less than 245° C.

Pressure is typically autogenous.

Contact (residence) time is typically about 0.5 to 10 hours.

In some embodiments, conversion of TCE is at least 15% or at least 30%, or at least 50%. In some embodiments, selectivity to 2320az is at least 80%, or at least 85%, or at least 90%.

Byproducts in the dimerization reaction may include tetrachloroethane isomers, tetrachlorobutadiene isomers, hexachlorobutene isomers, trichloroethylene oligomers. The product mixture comprising 2320az may further comprise E-1,1,2,3,4-pentachloro-1,3-butadiene or Z-1,1,2,3,4-pentachloro-1,3-butadiene. Thus, in one embodiment there is a composition comprising 1,1,2,4,4-pentachlorobuta-1,3-diene, E-1,1,2,3,4-pentachlorobuta-1,3-diene, and Z-1,1,2,3,4-pentachlorobuta-1,3-diene.

The process may further comprise recovering 2320az from the product mixture prior to use of the recovered 2320az as a starting material in a process to produce HCFC-346mdf, HCFC-336mfa, 1,1,1,4,4,4-hexafluoro-2-butyne and HFO-Z-1336mzz, for example, as set forth herein.

Processes for recovering 2320az from the product mixture may include one or any combination of purification techniques, such as distillation, that are known in the art. By "recovering" 2320az from the product mixture, a product comprising at least 95% or at least 97% or at least 99% 2320az is produced.

In certain embodiments, the process to produce 2320az may further comprise recovering trichloroethylene from the product mixture and recycling the recovered trichloroethylene to the dimerization process as set forth herein.

In certain embodiments, the process to produce 2320az may further comprise recovering hexachlorobutene isomers from the product mixture and recycling the recovered hexachlorobutene isomers to the dimerization process as set forth herein.

In certain embodiments, the process to produce 2320az may further comprise recovering pentachloroethane from the product mixture and recycling the recovered pentachloroethane to the dimerization process as set forth herein.

Other products, if present, such as E-1,1,2,3,4-pentachloro-1,3-butadiene and Z-1,1,2,3,4-pentachloro-1,3-butadiene may also be recovered.

Production of 2-Chloro-1,1,1,4,4,4-Hexafluorobutane (HCFC-346Mdf)

According to the process provided herein, there is provided a process comprising contacting 1,1,2,4,4-pentachlorobuta-1,3-diene (2320az) with HF in the presence of a catalyst in the liquid phase to produce a product mixture comprising HCFC-346mdf (346mdf).

Fluorination catalysts which may be used in the liquid phase process of the invention include those derived from Lewis acid catalysts such as metal halides. The halide may be chosen from fluoride, chloride, and bromide, or combination thereof. The metal halide may be transition metal halide or other metal halide. Transition metal chlorides include halides of titanium, zirconium, hafnium, tantalum, niobium, tin, molybdenum, tungsten and antimony. Other suitable metal halide catalysts include boron trichloride, boron trifluoride, and arsenic trifluoride In some embodiments, the liquid phase fluorination may be conducted in a reaction zone comprising any reaction vessel of appropriate size for the scale for the reaction. In some embodiments, the reaction zone is a reaction vessel comprised of materials which are resistant to corrosion. In some embodiments, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, New York) under the trademark Monel®, or vessels having fluoropolymers linings. In other embodiments, the reaction vessel may be made of other materials of construction including stainless steels, in particular those of the austenitic type, and copper-clad steel.

The molar ratio of HF to 2320az in some embodiments is from about 1 to about 35. In other embodiments, the molar ratio of HF to 2320az is from about 1 to about 25.

In some embodiments, the fluorination process is performed in at an elevated temperature, for example at a temperature in the range of 50 to 160° C. In some embodiments, the temperature may be greater than 100° C. In other embodiments, the temperature may be less than 150° C.

In some embodiments, the fluorination process is performed at a pressure in the range of 0 to 600 psi (0 to 4.1 MPa).

In some embodiments, residence time for the fluorination process may be from about 1 to about 25 hours. In other embodiments, residence time for the fluorination process may be from about 2 to about 10 hours. In other embodiments, residence time for the fluorination process may be from 4 to about 6 hours.

In some embodiments, the product mixture comprising 346mdf may further comprise one or more of 1,2-dichloro-1,1,4,4,4-pentafluorobutane, Z-1,1,1,4,4,4-hexafluoro-2-chloro-2-butene, E-1,1,1,4,4,4-hexafluoro-2-butene, and 1,1-dichloro-2,2,4,4,4-pentafluorobutane. In one embodiment, there is a composition comprising 2-chloro-1,1,1,4,4,4-hexafluorobutane (346mdf), 1,2-dichloro-1,1,4,4,4-pentafluorobutane (345mfd), Z-1,1,1,4,4,4-hexafluoro-2-chloro-2-butene (Z-1326mxz), E-1,1,1,4,4,4-hexafluoro-2-butene (E-1336mzz), and 1,1-dichloro-2,2,4,4,4-pentafluorobutane (345mfc).

In some embodiments, the product mixture is a composition comprising 346mdf comprises 1,1,1,4,4,4-hexafluorobutane (356mff), 1,1,1-trifluoro-2-trifluoromethylbutane (356mzz), Z-1,1,1,4,4,4-hexafluoro-2-chloro-2-butene (Z-1326mxz), E-1,1,1,4,4,4-hexafluoro-2-chloro-2-butene (E-1326mxz), Z-1,1,1,4,4,4-hexafluoro-2,3-dichlorobutene (Z-1316mxx), and E-1,1,1,4,4,4-hexafluoro-2,3-dichlorobutene (E-1316mxx). In an embodiment, the product mixture comprising 346mdf comprises greater than 0 and less than 2 weight % each of 356mff and 356mmz and greater than 0 and less than 3 weight % of Z-1326mxz, Z-1316mxx and E-1316mxx, and greater than 0 and less than 5 weight % of E-1326mxz. This composition is useful for producing 2,2-dichloro-1,1,1,4,4,4-hexafluorobutane (336mfa) as set forth herein.

In some embodiments, 346mdf is produced with a selectivity of greater than 90%, 92%, 94%, 95%, 96%, 97%, 98%, or 99%, with respect to other products.

The process may further comprise recovering 346mdf from the product mixture comprising 346mdf. Processes for recovering 346mdf include one or any combination of purification techniques, such as distillation, that are known in the art. By "recovering" 346mdf from the product mixture, a product comprising 346mdf comprising at least 98.5% or at least 99 or at least 99.5% 346mdf is produced.

In certain embodiments, the process to produce 346mdf may further comprise recovering 2320az from the product mixture and recycling the recovered 2320az to the fluorination process as set forth herein.

In some embodiments, the process for producing 346mdf as disclosed herein comprises (a') contacting trichloroethylene in the presence of a dimerization catalyst to produce a product mixture comprising 2320az; (a) contacting 2320az produced in step (a') with hydrogen fluoride in the liquid phase in the presence of a fluorination catalyst to produce a product mixture comprising 346mdf. Optionally, the 2320az is recovered after step (a') and prior to step (a).

In some embodiments, the process for producing 346mdf as disclosed herein comprises (a') contacting trichloroethylene in the presence of a dimerization catalyst and pentachloroethane to produce a product mixture comprising 2320az; (a) contacting 2320az produced in step (a') with hydrogen fluoride in the liquid phase in the presence of a fluorination catalyst to produce a product mixture comprising 346mdf. Optionally, the 2320az is recovered after step (a') and prior to step (a).

Variations on the elements of the process in steps (a') and (a) are disclosed herein above. The purity of 2320az is typically at least 97% before proceeding to step (a).

Production of 2,2-Dichloro-1,1,1,4,4,4-Hexafluorobutane (HCFC-336Mfa)

The present disclosure further provides a process comprising contacting 346mdf ($CF_3CH_2CHClCF_3$) with a chlorine source to produce a product mixture comprising 2,2-dichloro-1,1,1,4,4,4-hexafluorobutane ($CF_3CCl_2CH_2CF_3$, HCFC-336mfa, 336mfa). This process involves chlorination in which a chlorine source and 346mdf are reacted to produce a product mixture comprising the desired HCFC-336mfa product. The process may be performed in the liquid phase in a liquid medium or in the vapor phase. A catalyst is optional, but preferred. Alternatively, the process may use photoinitiation. An example of liquid medium is the 346mdf reactant itself.

Examples of suitable catalysts include Lewis acids, such as transition metal chlorides or aluminum chloride. Chlorination catalysts or photoinitation may be used in the liquid phase or vapor phase process.

Catalysts for this chlorination process in the liquid phase may be chosen from ferric chloride, chromium chloride, alumina chloride, cupric chloride and combinations of two or more of these. Catalysts for this chlorination process in the liquid phase may be chosen from ferric chloride, chromium chloride, alumina chloride, cupric chloride and combinations of two or more of these supported on carbon.

The chlorine source may be chosen from chlorine, N-chlorosuccinimide, t-butyl hypochlorite, oxalyl chloride, and sulfuryl chloride.

In an embodiment the reaction of 346mdf with a chlorine source is performed in the presence of a chlorination catalyst and the chlorine source is chlorine. In an alternative embodiment the reaction of 346mdf with a chlorine source is performed in the absence of any catalyst and the chlorine source is chlorine.

In an embodiment the reaction of 346mdf with a chlorine source is performed in the absence of a chlorination catalyst and the chlorine source is N-chlorosuccinimide, t-butyl hypochlorite, oxalyl chloride, and sulfuryl chloride.

The temperature and pressure conditions for the process are preferably selected to be effective to produce the 336mfa at high selectivity. In performing the process in the liquid phase, such as supplied by the 346mdf reactant, the process is preferably performed in a closed pressurizable reactor within which the pressure is sufficient pressure to maintain the 346mdf or the 336mfa process product in the liquid state. The pressure within the reactor may be or include autogenous pressure. The desired product HCFC-336mfa may be recovered from the reactor when the process is carried out in a liquid medium by purging unreacted chlorine, distilling off unreacted HCFC-346mdf, and filtering off the catalyst. When performed in the liquid phase, the catalyst may be filtered off if present in sufficiently high concentration that catalyst precipitates from product mixture prior to or during or after distillation. Alternatively, the catalyst may remain in the distillation heel.

A tubular reactor may be used to carry out the process in the vapor state (phase). Chlorination catalyst may be positioned within the reactor for effective contact with HCFC-346mdf and chlorine gaseous reactants simultaneously fed into the reactor at a temperature and residence time effective to produce the desired HCFC-336mfa reaction product in the selectivity desired. The temperature of the process is maintained by applying heat to the reactor. Preferably the temperature of the process is in the range of 100° C. to 200° C. The pressure within the tubular reactor is preferably about 0.1 to 1 MPa. The HCFC-336mfa reaction product may be recovered from the product mixture by distillation.

The chlorination of HCFC-346mdf preferably provides a selectivity to HCFC-336mfa of at least 85%, more preferably at least 90%, and most preferably, at least 95%, whether the reaction is carried out in the liquid phase or vapor phase.

Production of 1,1,1,4,4,4-hexafluoro-2-butyne

The present disclosure further provides a process comprising contacting HCFC-336mfa with base to produce a product mixture comprising 1,1,1,4,4,4-hexafluoro-2-butyne ($CF_3C\equiv CCF_3$) in a dehydrochlorination reaction. The base is preferably a basic aqueous medium. This reaction step is preferably performed in the presence of a catalyst. Preferably the basic aqueous medium comprises a solution of an alkali metal hydroxide or alkali metal halide salt or other base in water. Preferably the catalyst is a phase transfer catalyst. As used herein, phase transfer catalyst is intended to mean a substance that facilitates the transfer of ionic compounds between an organic phase and an aqueous phase. In this step, the organic phase comprises the HCFC-336mfa reactant, and the aqueous phase comprises the basic aqueous medium. The phase transfer catalyst facilitates the reaction of these dissimilar and incompatible components.

While various phase transfer catalysts may function in different ways, their mechanism of action is not determinative of their utility in the present invention provided that the phase transfer catalyst facilitates the dehydrochlorination reaction.

A preferred phase transfer catalyst is quaternary alkylammonium salt. In some embodiments, at least one alkyl group of the quaternary alkylammonium salt contains at least 8 carbons. An example of quaternary alkylammonium salt wherein three alkyl groups contain at least 8 carbon atoms includes trioctylmethylammonium chloride. Aliquat® 336 is a commercially available phase transfer catalyst which contains trioctylmethylammonium chloride. An example of quaternary alkylammonium salt wherein four alkyl groups contain at least 8 carbon atoms includes tetraoctylammonium salt. The anions of such salts may be halides such as chloride or bromide, hydrogen sulfate, or any other commonly used anion. Specific quaternary alkylammonium salts include tetraoctylammonium chloride, tetraoctylammonium hydrogen sulfate, tetraoctylammonium bromide, methytrioctylammonium chloride, methyltrioctylammonium bromide, tetradecylammonium chloride, tetradecylammonium bromide, and tetradodecylammonium chloride. According to such embodiments, the phase transfer catalyst and reaction conditions are effective to achieve conversion of HCFC-336mfa, preferably at least 50% per hour.

In other embodiments, the alkyl groups of the quaternary alkylammonium salt contain from 4 to 10 carbon atoms and a non-ionic surfactant is present in the aqueous basic medium. According to such embodiments, the phase transfer catalyst and reaction conditions are effective to achieve conversion of HCFC-336mfa preferably at least 20% per hour. The anions of quaternary alkylammonium salt wherein the alkyl group contains 4 to 10 carbon atoms may be halides such as chloride or bromide, hydrogen sulfate, or any other commonly used anion. Quaternary alkylammonium salts mentioned above may be used in this embodiment provided their alkyl groups contain 4 to 10 carbon atoms. Specific additional salts include tetrabutylammonium chloride, tetrabutylammonium bromide, and tetrabutylammonium hydrogen sulfate.

Preferred non-ionic surfactants include ethoxylated nonylphenol or an ethoxylated $C_{12}$-$C_{15}$ linear aliphatic alcohol. Non-ionic surfactants include Bio-soft® N25-9 and Makon® 10 useful in the present invention are obtainable from Stepan Company, Northfield, IL.

In some embodiments, the quaternary alkylammonium salt is added in an amount of from 0.5 mole percent to 2 mole percent of the HCFC-336mfa. In other embodiments, the quaternary alkylammonium salt is added in an amount of from 1 mole percent to 2 mole percent of the HCFC-336mfa. In yet other embodiments, the quaternary alkylammonium salts is added in an amount of from 1 mole percent to 1.5 mole percent of the HCFC-336mfa. In some embodiments, the quaternary alkylammonium salt is added in an amount of from 1 mole percent to 1.5 mole percent of the HCFC-336mfa and the weight of non-ionic surfactant added is from 1 to 2 times the weight of the quaternary alkylammonium salt. These amounts apply to each of the above-mentioned embodiments of the quaternary alkylammonium salt used.

In some embodiments, the reaction is preferably conducted at a temperature of from about 60 to 90° C., most preferably at 70° C.

A basic aqueous medium is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid in the basic aqueous solution is at least 90% water. In some embodiments the water is tap water; in other embodiments the water is deionized or distilled.

The base is chosen from hydroxide, oxide, carbonate, or phosphate salts of alkali, alkaline earth metals and mixtures thereof. In some embodiments, the base is chosen from lithium hydroxide, sodium hydroxide, potassium hydroxide, calcium hydroxide, magnesium oxide, calcium oxide, sodium carbonate, trisodium phosphate, disodium hydrogenphosphate, sodium dihydrogen phosphate, tripotassium phosphate, dipotassium hydrogenphosphate, potassium dihydrogen phosphate, and mixtures thereof.

These embodiments of basic aqueous medium and bases apply to all of the phase transition catalysts, amounts, and reaction conditions mentioned above. The selectivity to the formation of 1,1,1,4,4,4-hexafluoro-2-butyne is preferably at least 85%.

In some embodiments, the dehydrochlorination reaction of 336mfa to 1,1,1,4,4,4-hexafluoro-2-butyne is performed in the presence of an alkali metal halide salt. The alkali metal may be sodium or potassium. The halide may be chloride or bromide. A preferred alkali metal halide salt is sodium chloride. Without wishing to be bound by any particular theory, it is believed that the alkali metal halide salt stabilizes the phase transfer catalyst. Although the dehydrochlorination reaction itself produces alkali metal chloride, and in particular sodium chloride if sodium hydroxide is used as the base, addition of extra sodium chloride provides a further effect of increasing the yield of 1,1,1,4,4,4-hexafluoro-2-butyne. In some embodiments, the alkali metal halide is added at from about 25 to about 100 equivalents per mole of phase transfer catalyst. In other embodiments, the alkali metal halide is added at from about 30 to about 75 equivalents per mole of phase transfer catalyst. In yet other embodiments, the alkali metal halide is added at from about 40 to about 60 equivalents per mole of phase transfer catalyst. These amounts apply to each of the quaternary alkylammonium salts mentioned above.

The product 1,1,1,4,4,4-hexafluoro-2-butyne (boiling point −25° C.) may be recovered from the product mixture by distillation, wherein the butyne vaporizes from the aqueous medium and can then be condensed. In addition, the product mixture may also contain 1,1,1,4,4,4-hexafluoro-2-chloro-2-butene (HCFO-1326, Z-isomer, E-isomer, or a mixture thereof), which may be separated from the product mixture and recycled to the process step comprising contacting HCFC-336mfa with base to produce a product mixture comprising $CF_3C\equiv CCF_3$ in a dehydrochlorination reaction.

Production of Z-1,1,1,4,4,4-hexafluoro-2-butene

The present disclosure further provides a hydrogenation process comprising contacting 1,1,1,4,4,4-hexafluoro-2-butyne with hydrogen to produce a product mixture comprising Z-1,1,1,4,4,4-hexafluoro-2-butene (Z-1336mzz). This process is preferably performed in the presence of an alkyne-to-alkene catalyst.

In some embodiments the hydrogenation of 1,1,1,4,4,4-hexafluoro-2-butyne is performed as a batch process in the liquid phase.

In some embodiments the hydrogenation of 1,1,1,4,4,4-hexafluoro-2-butyne is performed as a continuous process in the vapor phase.

In some embodiments, an alkyne-to-alkene catalyst is a palladium catalyst, such as palladium dispersed on aluminum oxide or titanium silicate, doped with silver and/or a lanthanide. The loading of palladium dispersed on the aluminum oxide or titanium silicate is relatively low. In some embodiments, the palladium loading is from about 100 ppm to about 5000 ppm. In other embodiments, the palladium loading is from about 200 ppm to about 5000 ppm. In some embodiments, the palladium catalyst is doped with at least one of silver, cerium or lanthanum. In some embodiments, the mole ratio of cerium or lanthanum to palladium is from about 2:1 to about 3:1. In some embodiments the mole ratio of silver to palladium is about 0.5:1.0.

Other embodiments of alkyne-to-alkene catalyst is Lindlar catalyst, which is a heterogeneous palladium catalyst on a calcium carbonate support, which has been deactivated or conditioned with a lead compound. The lead compound may be lead acetate, lead oxide, or any other suitable lead compound. In some embodiments, the catalyst is produced by reduction of a palladium salt in the presence of a slurry of calcium carbonate, followed by the addition of the lead compound. In some embodiments, the palladium salt in palladium chloride.

In other embodiments, the Lindlar catalyst is further deactivated or conditioned with quinoline. The amount of palladium on the support is typically about 5% by weight but may be any catalytically effective amount. In other embodiments, the amount of palladium on the support in the Lindlar catalyst is greater than 5% by weight. In yet other embodiments, the amount of palladium on the support may be from about 5% by weight to about 1% by weight.

In some embodiments, the amount of the catalyst used is from about 0.5% by weight to about 4% by weight of the amount of the 1,1,1,4,4,4-hexafluoro-2-butyne. In other embodiments, the amount of the catalyst used is from about 1% by weight to about 3% by weight of the amount of the butyne. In yet other embodiments, the amount of the catalyst used is from about 1% to about 2% by weight of the amount of the butyne.

In some embodiments, this reaction step is a batch reaction and is performed in the presence of a solvent. In one such embodiment, the solvent is an alcohol. Typical alcohol solvents include ethanol, i-propanol and n-propanol. In other embodiments, the solvent is a fluorocarbon or hydrofluorocarbon. Typical fluorocarbons or hydrofluorocarbons include 1,1,1,2,2,3,4,5,5,5-decafluoropentane and 1,1,2,2,3,3,4-heptafluorocyclopentane.

In some embodiments, reaction of the 1,1,1,4,4,4-hexafluoro-2-butyne with hydrogen is preferably performed with addition of hydrogen in portions, with increases in the pressure of the vessel of no more than about 100 psi (0.69 MPa) with each addition. In other embodiments, the addition of hydrogen is controlled so that the pressure in the vessel increases no more than about 50 psi (0.35 MPa) with each addition. In some embodiments, after enough hydrogen has been consumed in the hydrogenation reaction to convert at least 50% of the butyne to Z-1336mzz, hydrogen may be added in larger increments for the remainder of the reaction. In other embodiments, after enough hydrogen has been consumed in the hydrogenation reaction to convert at least 60% of the butyne to the desired butene, hydrogen may be added in larger increments for the remainder of the reaction. In yet other embodiments, after enough hydrogen has been consumed in the hydrogenation reaction to convert at least 70% of the butyne to desired butene, hydrogen may be added in larger increments for the remainder of the reaction. In some embodiments, the larger increments of hydrogen addition may be 300 psi (2.07 MPa). In other embodiments, the larger increments of hydrogen addition may be 400 psi (2.76 MPa).

In some embodiments, the molar ratio is about 1 mole of hydrogen to about 1 mole of 1,1,1,4,4,4-hexafluoro-2-butyne. In other embodiments, the molar ratio is from about 0.9 mole to about 1.3 mole, hydrogen to butyne. In yet other embodiments, the amount of hydrogen added is from about 0.95 mole of hydrogen to about 1.1 moles of butyne. In yet other embodiments, the amount of hydrogen added is from about 0.95 moles of hydrogen to about 1.03 moles of butyne.

In some embodiments, the hydrogenation is performed at ambient temperature (15° C. to 25° C.). In other embodiments, the hydrogenation is performed at above ambient temperature. In yet other embodiments, the hydrogenation is performed at below ambient temperature. In yet other embodiments, the hydrogenation is performed at a temperature of below about 0° C.

In an embodiment of a continuous process, a mixture of 1,1,1,4,4,4-hexafluoro-2-butyne and hydrogen is passed through a reaction zone containing the catalyst. A reaction vessel, e.g., a metal tube, may be used, packed with the catalyst to form the reaction zone. In some embodiments, the molar ratio of hydrogen to the butyne is about 1:1. In other embodiments of a continuous process, the molar ratio of hydrogen to the butyne is less than 1:1. In yet other embodiments, the molar ratio of hydrogen to the butyne is about 0.67:1.0.

In some embodiments of a continuous process, the reaction zone is maintained at ambient temperature. In other embodiments of a continuous process, the reaction zone is maintained at a temperature of 30° C. In yet other embodiments of a continuous process, the reaction zone is maintained at a temperature of about 40° C.

In some embodiments of a continuous process, the flow rate of 1,1,1,4,4,4-hexafluoro-2-butyne and hydrogen is maintained so as to provide a residence time in the reaction zone of about 30 seconds. In other embodiments of a continuous process, the flow rate of the butyne and hydrogen is maintained so as to provide a residence time in the reaction zone of about 15 seconds. In yet other embodiments of a continuous process, the flow rate of butyne and hydrogen is maintained so as to provide a residence time in the reaction zone of about 7 seconds.

It will be understood, that residence time in the reaction zone is reduced by increasing the flow rate of 1,1,1,4,4,4-hexafluoro-2-butyne and hydrogen into the reaction zone. As the flow rate is increased this will increase the amount of butyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

The conditions of the contacting step, including the choice of catalyst, are preferably selected to produce Z-1336mzz at a selectivity of at least 85%, more preferably at least 90%, and most preferably at least 95%.

In some embodiments, upon completion of a batch-wise or continuous hydrogenation process, the Z-1336mzz may be recovered through any conventional process, including for example, fractional distillation. Unconverted hexafluoro-2-butyne may be recovered and recycled to the hydrogenation process. In other embodiments, upon completion of a batch-wise or continuous hydrogenation process, the Z-1336mzz is of sufficient purity to not require further purification steps.

EXAMPLES

Materials

Trichloroethylene, ferric chloride, pentachloroethane (HCC-120), chlorine, $TaCl_5$, and tetra-n-butylammonium bromide (TBAB), and trioctylmethylammonium chloride (Aliquat® 336) are available from Sigma Aldrich, St. Louis, MO. Hydrogen fluoride was purchased from Synquest Labs, Inc., Alachua, FL. Makon® 10 nonionic surfactant is available from Stepan Company, Northfield, IL.

GC analysis for Examples 1-4 was performed using Agilent® 5975GC, RESTEK Rtx-1 column.

Example 1: Preparation of
1,1,2,4,4-pentachlorobuta-1,3-diene (HCC-2320az)

Trichloroethylene (100 g, 0.76 mol) was added to a shaker tube containing 30 mg anhydrous $FeCl_3$. The reaction mixture was heated at 230° C. for 2 hrs. The reactor content was cooled to room temperature and analyzed by GC to determine the conversion and selectivity. Results are provided in Table 1.

Example 2: Preparation of
1,1,2,4,4-pentachlorobuta-1,3-diene (HCC-2320az)

Trichloroethylene (100 g, 0.76 mol) was added to a shaker tube containing 1 g iron wire. The reaction mixture was heated at 230° C. for 2 hrs. The reactor content was cooled to room temperature and analyzed by GC to determine the conversion and selectivity. Results are provided in Table 1.

Example 3: Preparation of
1,1,2,4,4-pentachlorobuta-1,3-diene (HCC-2320az)

Trichloroethylene (100 g, 0.76 mol) was added to a shaker tube containing 20 mg anhydrous $FeCl_3$ and 1 g HCC-120. The reaction mixture was heated at 230° C. for 2 hrs. The reactor content was cooled to room temperature and analyzed by GC to determine the conversion and selectivity. Results are provided in Table 1.

Example 4: Preparation of
1,1,2,4,4-pentachlorobuta-1,3-diene (HCC-2320az)

Trichloroethylene (100 g, 0.76 mol) was added to a shaker tube containing 1 g iron wire and 1 g HCC-120. The reaction mixture was heated at 230° C. for 2 hrs. The reactor content was cooled to room temperature and analyzed by GC to determine the conversion and selectivity. Results are provided in Table 1.

TABLE 1

Trichloroethylene Dimerization to 2320az

| Example | Catalyst | Time (hours) | Conversion/ Selectivity (%) |
|---|---|---|---|
| 1 | FeCl$_3$ (30 mg) | 16 | 26.9/81.6 |
| 2 | Fe wire (1 g) | 8 | 28.0/86.7 |
| 3 | FeCl$_3$ (20 mg)/HCC-120 (1 g) | 2 | 35.4/84.3 |
| 4 | Fe wire (1 g)/HCC-120 (1 g) | 2 | 32.3/87.4 |

As can be seen from Table 1, the presence of HCC-120 increases conversion rate of trichloroethylene to 2320az when using FeCl$_3$ or Fe wire catalyst.

Example 5: Preparation of 2-chloro-1,1,1,4,4,4-hexafluorobutane (HCFC-346mdf)

TaCl$_5$ (12.5 g) was added to a 210 mL Hastelloy C reactor, followed by HF (49 g). The reaction mixture was heated to 150° C. for 1 hour and cooled to 0° C. HCC-2320az (26 g) was added to the reactor and the reaction was reheated to 130° C. The reaction rate was indicated by pressure increase. The level-off pressure means the completion of the reaction. After aqueous work up and phase separation, the product mixture was analyzed by GC and showed 100% conversion of starting material, and 98% selectivity to product HCFC-346mdf.

Example 6: Preparation of 2,2-dichloro-1,1,1,4,4,4-hexafluorobutane (HCFC-336mfa)

A Hastelloy tube (½ inch OD) with a 12" heated reaction zone is used in the following reaction. The reaction zone is preheated to 300° C. HCFC-346mdf is fed at 3.1 sccm (5.2×10$^{-8}$ m$^3$/sec) and chlorine gas is fed at 11.6 sccm (1.9×10$^{-7}$ m$^3$/sec). No catalyst is present. Part of the reactor effluent is passed through a series of valves and analyzed by GCMS. After 13 hours of continuous operation, the product contains 90% 2,2-dichloro-1,1,1,4,4,4-hexafluorobutane (HCFC-336mfa).

Example 7: Preparation of 1,1,1,4,4,4-hexafluoro-2-butyne

Example 7 demonstrates the conversion of HCFC-336mfa to 1,1,1,4,4,4-hexafluoro-2-butyne in the presence of Aliquat® 336 quaternary ammonium salt.

NaOH aqueous solution (22 mL, 0.22 mol) is added to HCFC-336mfa (23.5 g, 0.1 mol) and water (5.6 mL) in the presence of Aliquat® 336 ammonium salt (0.53 g, 0.001325 mol) at room temperature. The reaction temperature is raised to 70° C. after the addition, and gas chromatography is used to monitor the reaction. The reaction is completed after 2 hour and 1,1,1,4,4,4-hexafluorobutyne is collected in a dry ice trap.

Example 8: Preparation of 1,1,1,4,4,4-hexafluoro-2-butyne

Example 8 demonstrates the conversion of HCFC-336mfa to 1,1,1,4,4,4-hexafluoro-2-butyne in the presence of tetrabutylammonium bromide and a nonionic surfactant.

NaOH aqueous solution (22 mL, 0.22 mol) is added to HCFC-336mfa (23.5 g, 0.1 mol) and water (5.6 mL) in the presence of tetrabutylammonium bromide (0.45 g, 0.001325 mol) and Makon® 10 nonionic surfactant (0.7 g) at room temperature. The reaction temperature is raised to 70° C. after the addition, and gas chromatography is used to monitor the reaction. The reaction is completed after 4.5 hours and 1,1,1,4,4,4-hexafluorobutyne is collected in a dry ice trap.

Example 9: Preparation of Z-1,1,1,4,4,4-hexafluoro-2-butene 1,1,1,4,4,4-Hexafluoro-2-butyne was reacted with hydrogen to produce the desired Z-isomer of 1,1,1,4,4,4-hexafluoro-2-butene by the following procedure: 5 g of Lindlar (5% Pd on CaCO$_3$ poisoned with lead) catalyst was charged in 1.3 L rocker bomb. 480 g (2.96 mol) of hexafluoro-2-butyne was charged in the rocker. The reactor was cooled (−78° C.) and evacuated. After the bomb was warmed to room temperature, H$_2$ was added slowly, by increments which did not exceed Δp=50 psi (0.35 MPa). A total of 3 moles H$_2$ were added to the reactor. A gas chromatographic analysis of the crude product indicated the mixture consisted of CF$_3$C≡CCF$_3$ (0.236%), trans-isomer E-CF$_3$CH=CHCF$_3$ (0.444%), saturated CF$_3$CH$_2$CH$_2$CF$_3$ (1.9%) CF$_2$=CHCl, impurity from starting butyne, (0.628%), cis-isomer Z—CF$_3$CH=CHCF$_3$ (96.748%).

Distillation of the crude product afforded 287 g (59% yield) of 100% pure cis-CF$_3$CH=CHCF$_3$ (boiling point 33.3° C.). MS: 164 [MI], 145 [M-19], 95 [CF$_3$CH=CH], 69 [CF$_3$]. NMR H$^1$: 6.12 ppm (multiplet), F$^{19}$: −60.9 ppm (triplet J=0.86 Hz). The selectivity of this reaction to the formation of the Z-isomer was 96.98%. The Z-isomer was recovered by distillation.

Other Embodiments

1. In some embodiments, the present disclosure provides a process for preparing 2,2-dichloro-1,1,1,4,4,4-hexafluorobutane comprising: contacting 2-chloro-1,1,1,4,4,4-hexafluorobutane with a chlorine source.
2. In some embodiments, 2-chloro-1,1,1,4,4,4-hexafluorobutane is produced by contacting 1,1,2,4,4-pentachlorobuta-1,3-diene with HF in the liquid phase in the presence of a fluorination catalyst.
3. In some embodiments, 1,1,2,4,4-pentachlorobuta-1,3-diene is produced by contacting trichloroethylene in the presence of a dimerization catalyst.
4. The process recited in any of the embodiments, 1, 2, or 3 further comprises contacting 2,2-dichloro-1,1,1,4,4,4-hexafluorobutane with a basic aqueous medium to produce a product comprising 1,1,1,4,4,4-hexafluoro-2-butyne.
5. Any of the embodiments recited in embodiment 4 further comprises contacting 1,1,1,4,4,4-hexafluoro-2-butyne with hydrogen to produce a product comprising Z-1,1,1,4,4,4-hexafluoro-2-butene.
6. Any of the embodiments recited in embodiments 1, 2, 3, 4 or 5 further comprises recovering 2,2-dichloro-1,1,1,4,4,4-hexafluorobutane.
7. Any of the embodiments recited in embodiments 2, 3, 4, 5 or 6 further comprises recovering 2-chloro-1,1,1,4,4,4-hexafluorobutane.
8. Any of the embodiments recited in embodiments 3, 4, 5, 6 or 7 further comprises recovering 1,1,2,4,4-pentachlorobuta-1,3-diene.

9. Any of the embodiments recited in embodiments 4, 5, 6, 7 or 8 further comprises recovering 1,1,1,4,4,4-hexafluoro-2-butyne.

10. Any of the embodiments recited in embodiments 5, 6, 7, 8 or 9 further comprises recovering Z-1,1,1,4,4,4-hexafluoro-2-butene.

11. In some embodiments, a process for producing Z-1,1,1,4,4,4-hexafluoro-2-butene comprises:
(a) contacting 1,1,2,4,4-pentachlorobuta-1,3-diene with HF in the liquid phase in the presence of a fluorination catalyst to produce a product mixture comprising 2-chloro-1,1,1,4,4,4-hexafluorobutane;
(b) contacting 2-chloro-1,1,1,4,4,4-hexafluorobutane with chlorine to produce a product mixture comprising 2,2-dichloro-1,1,1,4,4,4-hexafluorobutane;
(c) contacting 2,2-dichloro-1,1,1,4,4,4-hexafluorobutane with base to produce a product mixture comprising 1,1,1,4,4,4-hexafluoro-2-butyne; and
(d) contacting 1,1,1,4,4,4-hexafluoro-2-butyne with hydrogen to produce a product mixture comprising Z-1,1,1,4,4,4-hexafluoro-2-butene.

12. In some embodiments, the chlorine source recited in embodiment 1 is chlorine.

13. In some embodiments, the catalyst in embodiment 2 comprises a metal halide.

14. Embodiment 2 wherein 1,1,2,4,4-pentachlorobuta-1,3-diene is produced by contacting trichloroethylene in the presence of a dimerization catalyst and pentachloroethane.

15. Any of the embodiments recited in embodiments 1, 2, or 3 further comprising contacting 2,2-dichloro-1,1,1,4,4,4-hexafluorobutane with a basic aqueous medium and a phase transfer catalyst to produce a product comprising 1,1,1,4,4,4-hexafluoro-2-butyne.

16. Embodiment 5 wherein 1,1,1,4,4,4-hexafluoro-2-butyne is contacted with hydrogen in the presence of an alkyne-to-alkene catalyst to produce a product comprising Z-1,1,1,4,4,4-hexafluoro-2-butene.

17. Embodiment 16 wherein the alkyne-to-alkene catalyst is a palladium catalyst at a concentration of 100-5000 ppm dispersed over aluminum oxide, silicon carbide, or titanium silicates with a Ag or lanthanide poison.

18. Embodiment 1 wherein the chlorine source is $Cl_2$ and the process is performed in the absence of a catalyst.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A process for producing 2,2-dichloro-1,1,1,4,4,4-hexafluorobutane comprising: contacting 2-chloro-1,1,1,4,4,4-hexafluorobutane with a chlorine source.

2. The process of claim 1 wherein the chlorine source is $Cl_2$ and the process is performed in the absence of a catalyst.

3. The process of claim 1 further comprising recovering 2,2-dichloro-1,1,1,4,4,4-hexafluorobutane.

4. The process of claim 1 wherein 2-chloro-1,1,1,4,4,4-hexafluorobutane is produced by contacting 1,1,2,4,4-pentachlorobuta-1,3-diene with HF in the liquid phase in the presence of a fluorination catalyst.

5. The process of claim 4 further comprising recovering 2-chloro-1,1,1,4,4,4-hexafluorobutane.

6. The process of claim 4 wherein 1,1,2,4,4-pentachlorobuta-1,3-diene is produced by contacting trichloroethylene in the presence of a dimerization catalyst.

7. The process of claim 4 wherein 1,1,2,4,4-pentachlorobuta-1,3-diene is produced by contacting trichloroethylene in the presence of a dimerization catalyst and pentachloroethane.

8. The process of claim 1 further comprising contacting 2,2-dichloro-1,1,1,4,4,4-hexafluorobutane with base to produce a product mixture comprising 1,1,1,4,4,4-hexafluoro-2-butyne.

9. The process of claim 8 further comprising recovering 1,1,1,4,4,4-hexafluoro-2-butyne.

10. The process of claim 8 further comprising contacting 1,1,1,4,4,4-hexafluoro-2-butyne with hydrogen to produce a product mixture comprising Z-1,1,1,4,4,4-hexafluoro-2-butene.

11. The process of claim 10 further comprising recovering Z-1,1,1,4,4,4-hexafluoro-2-butene.

12. The process of claim 10 wherein 1,1,1,4,4,4-hexafluoro-2-butyne is contacted with hydrogen in the presence of an alkyne-to-alkene catalyst, wherein the alkyne-to-alkene catalyst is a palladium catalyst at a concentration of 100-5000 ppm dispersed over aluminum oxide, silicon carbide, or titanium silicates with a Ag or lanthanide poison.

13. A process for producing Z-1,1,1,4,4,4-hexafluoro-2-butene comprising:
(a) contacting trichloroethylene with a dimerization catalyst to produce a product mixture comprising 1,1,2,4,4-pentachlorobuta-1,3-diene;
(b) contacting 1,1,2,4,4-pentachlorobuta-1,3-diene with HF in the liquid phase in the presence of a fluorination catalyst in the liquid phase to form a product mixture comprising 2-chloro-1,1,1,4,4,4-hexafluorobutane,
(c) contacting 2-chloro-1,1,1,4,4,4-hexafluorobutane with a chlorine source to form a product mixture comprising 2,2-dichloro-1,1,1,4,4,4-hexafluorobutane;
(d) contacting 2,2-dichloro-1,1,1,4,4,4-hexafluorobutane with base to produce a product mixture comprising 1,1,1,4,4,4-hexafluoro-2-butyne; and
(e) contacting 1,1,1,4,4,4-hexafluoro-2-butyne with hydrogen produce a product mixture comprising Z-1,1,1,4,4,4-hexafluoro-2-butene.

14. The process of claim 13 further comprising recovering Z-1,1,1,4,4,4-hexafluoro-2-butene from the product mixture of step (e).

15. A composition comprising 2-chloro-1,1,1,4,4,4-hexafluorobutane, Z-1,1,1,4,4,4-hexafluoro-2-chloro-2-butene, 1,2-dichloro-1,1,4,4,4-pentafluorobutane, E-1,1,1,4,4,4-hexafluoro-2-butene, and 1,1-dichloro-2,2,4,4,4-pentafluorobutane.

16. A composition comprising 2-chloro-1,1,1,4,4,4-hexafluorobutane, 1,1,1,4,4,4-hexafluorobutane, 1,1,1-trifluoro-2-trifluoromethylbutane, Z-1,1,1,4,4,4-hexafluoro-2-chloro-2-butene, E-1,1,1,4,4,4-hexafluoro-2-chloro-2-butene, Z-1,1,1,4,4,4-hexafluoro-2,3-dichlorobutene, and E-1,1,1,4,4,4-hexafluoro-2,3-dichlorobutene.

* * * * *